United States Patent [19]

Iwakura et al.

[11] Patent Number: 5,994,606
[45] Date of Patent: Nov. 30, 1999

[54] METHOD FOR DEHYDROGENATION OF HYDROCARBON

[75] Inventors: Tomoatsu Iwakura; Makoto Takiguchi, both of Ami-machi, Japan

[73] Assignee: Mitsubishi Chemical Corporation, Tokyo, Japan

[21] Appl. No.: 08/854,134

[22] Filed: May 8, 1997

Related U.S. Application Data

[63] Continuation-in-part of application No. 08/610,632, Mar. 4, 1996, abandoned.

[30] Foreign Application Priority Data

| Mar. 8, 1995 | [JP] | Japan | 7-048740 |
| Mar. 28, 1995 | [JP] | Japan | 7-069855 |
| May 16, 1995 | [JP] | Japan | 7-117053 |
| May 16, 1995 | [JP] | Japan | 7-117054 |
| May 16, 1995 | [JP] | Japan | 7-117055 |

[51] Int. Cl.[6] .................................. C07C 5/333
[52] U.S. Cl. .................... 585/660; 208/134; 208/137; 208/138; 585/654; 585/659
[58] Field of Search .................... 208/137, 138, 208/134; 585/654, 660, 659

[56] References Cited

U.S. PATENT DOCUMENTS

| 2,403,052 | 6/1946 | Cole et al. ............... 585/662 |
| 2,437,531 | 3/1948 | Huffman ................ 208/136 |
| 2,846,363 | 9/1958 | Folkins et al. ............ 208/136 |
| 4,124,649 | 11/1978 | Rausch ................. 260/666 A |
| 4,381,257 | 4/1983 | Antos ................... 252/466 B |
| 4,435,607 | 3/1984 | Imai ...................... 585/443 |
| 4,479,902 | 10/1984 | Rosen ...................... 260/409 |
| 5,001,291 | 3/1991 | Holt et al. .................. 585/319 |
| 5,527,979 | 6/1996 | Agaskar et al. .............. 585/659 |
| 5,593,935 | 1/1997 | Goulinski et al. ............ 502/339 |

FOREIGN PATENT DOCUMENTS

| 0 089 183 | 9/1983 | European Pat. Off. . |
| 0 336 622 | 10/1989 | European Pat. Off. . |
| 0 501 265 | 9/1992 | European Pat. Off. . |
| 0 505 863 | 9/1992 | European Pat. Off. . |

OTHER PUBLICATIONS abstract of (GB 2297043 A1), author:Hagemeyer et al, Jul. 24, 1996.

*Primary Examiner*—Walter D. Griffin
*Assistant Examiner*—Nadine Preisch
*Attorney, Agent, or Firm*—Oblon, Spivak, McClelland, Maier & Neustadt, P.C.

[57] ABSTRACT

A method for dehydrogenation of a hydrocarbon, which comprises selectively oxidizing hydrogen in a gas mixture which is obtained by subjecting a feed hydrocarbon to a dehydrogenation reaction in the presence of a dehydrogenation catalyst and which comprises a dehydrogenated hydrocarbon, an unreacted feed hydrocarbon and hydrogen, by contacting the gas mixture with an oxygen-containing gas in the presence of an oxidation catalyst, and further subjecting a hydrocarbon-containing gas obtained by the oxidation reaction to a dehydrogenation reaction, wherein a catalyst comprising a component having platinum and/or palladium supported on a carrier obtained by calcining at least one member selected from the group consisting of tin oxide, titanium oxide, tantalum oxide and niobium oxide, at a temperature of from 800° C. to 1,500° C., is used as the oxidation catalyst.

7 Claims, No Drawings

METHOD FOR DEHYDROGENATION OF HYDROCARBON

This application is a continuation-in-part of U.S. patent application Ser. No. 08/610,632 filed Mar. 4, 1996, now abandoned, and incorporated entirely herein by reference.

BACKGROUND OF THE INVENTION

1. Field of the Invention

The present invention relates to a method for dehydrogenation, which comprises selectively oxidizing hydrogen present in a gas mixture formed at the time of dehydrogenation of a hydrocarbon to produce a dehydrogenated hydrocarbon.

2. Discussion of Background

A process for producing a dehydrogenated hydrocarbon by dehydrogenation of a hydrocarbon, has been disclosed in many literatures. For example, a process for preparing styrene by dehydrogenation of methylbenzene is industrially practiced by means of an iron-type catalyst. However, a dehydrogenation reaction is usually subject to a restriction of equilibrium, whereby it is difficult to attain a good yield. Further, the dehydrogenation reaction is an endothermic reaction, and if the reaction is carried out by an insulated reactor, the reaction temperature decreases as the reaction proceeds, whereby it is difficult to obtain the desired product in good yield.

Under these circumstances, some methods have already been proposed. For example, UK Patent No. 1,404,641 discloses a process and a catalyst for selectively oxidizing hydrogen in a gas mixture comprising unreacted methylbenzene, styrene and hydrogen after the dehydrogenation of ethylbenzene. This method is effective for the preparation of styrene, but A-type zeolite or alumina having platinum supported thereon is used as a catalyst for selective oxidation of hydrogen, and its performance is not necessarily satisfactory.

Also U.S. Pat. No. 4,565,898 discloses a method of using a catalyst having e.g. platinum tin and lithium supported on alumina for a similar process. However, this catalyst is supported also on alumina, and its performance is not fully satisfactory.

Further, Japanese Unexamined Patent Publications No. 89945/1983 and No. 298678/1994 disclose a method for selectively oxidizing hydrogen in a gas mixture comprising styrene, ethylbenzene and hydrogen, formed by the dehydrogenation reaction of ethylbenzene, by means of a catalyst containing tin oxide, or tin oxide and an alkali metal. This catalyst is noteworthy as a catalyst employing no platinum, but its performance is not necessarily adequate.

EP-A-0336622 discloses a similar process using a catalyst having palladium carried on tin oxide. However, according to this process, there was a problem of by-producing benzene and toluene and losing ethylbenzene and styrene.

As described above, conventional catalysts are not satisfactory in their performance as catalysts for selectively oxidizing hydrogen in a gas mixture comprising an unreacted hydrocarbon, a hydrogenated hydrocarbon and hydrogen, formed by the dehydrogenation reaction of a hydrocarbon.

SUMMARY OF THE INVENTION

The present invention provides a method for dehydrogenation of a hydrocarbon, which comprises selectively oxidizing hydrogen in a gas mixture which is obtained by subjecting a feed hydrocarbon to a dehydrogenation reaction in the presence of a dehydrogenation catalyst and which comprises a dehydrogenated hydrocarbon, an unreacted feed hydrocarbon and hydrogen, by contacting the gas mixture with an oxygen-containing gas in the presence of an oxidation catalyst, and further subjecting a hydrocarbon-containing gas obtained by the oxidation reaction to a dehydrogenation reaction, wherein a catalyst comprising a component having platinum and/or palladium supported on a carrier obtained by calcining at least one member selected from the group consisting of tin oxide, titanium oxide, tantalum oxide and niobium oxide, at a temperature of from 800° C. to 1,500° C., is used as the oxidation catalyst.

DETAILED DESCRIPTION OF THE INVENTION

Now, the present invention will be described in detail with reference to the preferred embodiments.

The catalyst for selective oxidation of hydrogen to be used in the method of the present invention is a catalyst containing tin oxide, titanium oxide, tantalum oxide or niobium oxide having platinum and/or palladium supported thereon.

The oxide carrier to be used in the present invention, can be prepared by a suitable method which is commonly employed for the preparation of catalysts. For example, an aqueous alkaline solution such as aqueous ammonia, an alkali metal carbonate solution or an alkali metal hydrogencarbonate solution may be added to an aqueous solution of a salt of tin, titanium, tantalum or niobium with stirring, or water may be added to a solution of an organic salt of tin, titanium, tantalum or niobium with stirring, to form a precipitate of a hydroxide, which is then collected by filtration and washed. This hydroxide is dried and then calcined at a proper temperature to convert it into an oxide, for example, at a temperature of from 800 to 1,500° C., preferably from 800 to 1,200° C. The oxide thus prepared may be tabletted or extrusion-molded as the case requires. The starting material salt of tin, titanium, tantalum or niobium is not particularly limited, and a chloride, a nitrate, a sulfate, an organic salt or a hydroxide of such a metal may be employed. Further, such a salt may directly be calcined to obtain a catalyst carrier in the form of an oxide.

As a method for supporting platinum and/or palladium on such an oxide carrier, a method may, for example, be mentioned in which an aqueous solution of a salt of platinum or palladium is impregnated to the oxide after calcination, followed by drying and calcining at a temperature of from 50 to 1,000° C. The starting material salt of platinum or palladium is not particularly limited, and a halide, a hydroxide, a sulfate or an organic salt thereof may, for example, be employed.

The amount of platinum or palladium supported, is usually from 0.01 to 10 wt %, preferably from 0.05 to 5 wt %, based on the oxide carrier. If the amount supported is too small, the catalytic activity for the oxidation reaction tends to be low. On the other hand, even if the amount supported is increased beyond the above range, no substantial further effects to the reaction will be obtained, and such will be disadvantageous from the viewpoint of the costs.

The oxidation catalyst of the present invention is useful for a reaction for selectively oxidizing hydrogen in a gas mixture containing hydrogen and a hydrocarbon by contacting the gas mixture with an oxygen-containing gas. Such a reaction is conducted preferably within a temperature range of from 300 to 800° C., more preferably from 400 to 700°

C. If the temperature is too high, the selectivity for hydrogen decreases, and combustion of the hydrocarbon increases, such being undesirable. If the temperature is too low, the activity tends to be low, although the selectivity may not substantially be affected.

A specific example of the gas mixture containing hydrogen and a hydrocarbon may be a gas mixture which is obtained by subjecting a feed hydrocarbon to a dehydrogenation reaction in the presence of a dehydrogenation catalyst and which comprises a dehydrogenated hydrocarbon, an unreacted feed hydrocarbon and hydrogen.

The oxygen-containing gas may, for example, be a gas containing from 1 to 100% of molecular oxygen. Specifically, air, oxygen-enriched air or air diluted with an inert gas may suitably be employed. Further, steam may be incorporated into the oxgen-containing gas.

A typical process to which the selective oxidation catalyst and the selective oxidation method of the present invention may be applied, is as follows.

In a first reaction zone, a dehydrogenation reaction of a feed hydrocarbon is carried out by a dehydrogenation catalyst, and then, a gas mixture containing a dehydrogenated hydrocarbon, an unreacted feed hydrocarbon and hydrogen, discharged from this first reaction zone, will be sent to a second reaction zone. In this second reaction zone, selective oxidation of hydrogen is carried out in the presence of the selective oxidation catalyst of the present invention by means of an oxygen-containing gas introduced anew, whereby the temperature once lowered by the first dehydrogenation reaction as an endothermic reaction will be raised, and the restriction by equilibrium of the dehydrogenation reaction will be eliminated by the consumption of hydrogen. Further, the gas discharged from this second reaction zone will be sent to a third dehydrogenation reaction zone which is similar to the first reaction zone, and dehydrogenation of an unreacted hydrocarbon will be carried out. As the temperature required for the reaction has already been recovered and the restriction by equilibrium has already been eliminated in the second reaction zone, a higher yield can be attained in the third dehydrogenation reaction zone.

If necessary, the reaction can be carried out by further adding a combination of the above selective oxidation reaction zone and the dehydrogenation reaction zone.

It is common to conduct a dehydrogenation reaction in the presence of steam. Also in the above reaction process, steam may be present.

As a typical specific example of the above dehydrogenation process, a dehydrogenation process of ethylbenzene may, for example, be mentioned. Namely, for example, a gas mixture of ethylbenzene and steam is sent to a first reaction zone, where an iron-type catalyst comprising iron and an alkali metal as the main active components, is present, and a dehydrogenation reaction is carried out at a temperature within a range of from 500 to 800° C. under a pressure within a range of from 0.05 to 10 atm. Then, a gas mixture of an unreacted ethylbenzene, formed styrene, hydrogen and steam, will be sent to a second reaction zone. In the second reaction zone, selective oxidation of hydrogen is carried out in the presence of the oxidation catalyst of the present invention by means of an oxygen-containing gas introduced anew. Then, this reaction gas is sent to a third reaction zone, where dehydrogenation of unreacted ethylbenzene is carried out again by an iron-type catalyst, to obtain styrene in good yield.

As mentioned above, according to the method of the present invention, the restriction by equilibrium will be removed, and the decrease of the reaction temperature can be supplemented, whereby it is possible to obtain styrene in a yield substantially higher as compared with conventional dehydrogenation reactions.

Now, the present invention will be described in further detail with reference to Examples. However, it should be understood that the present invention is by no means restricted to such specific Examples.

EXAMPLE 1

Preparation of a Catalyst 3N aqueous ammonia was gradually added to an aqueous stannous chloride solution with stirring to form a precipitate of a hydroxide. When the pH exceeded 7, addition of aqueous ammonia was stopped. Then, the formed precipitate of tin hydroxide was collected by filtration and washed with water. The obtained precipitate of tin hydroxide was dried in a drier at 120° C. overnight. The dried precipitate was calcined in a muffle furnace at 600° C. for 2 hours. A small amount of water was added to this calcined product, followed by extrusion molding to obtain pellets having an average size of 3 mm in diameter×10 mm, which were again calcined at 1,000° C. for 3 hours. The calcined product was further pulverized to obtain tin oxide of a particle size of from 0.85 to 1.0 mm. 5.2 g of the tin oxide of from 10 to 20 mesh was immersed in 2 g of an aqueous solution of chloroplatinic acid ($H_2PtCl_6 \cdot 6H_2O$) containing 0.0021 g of platinum and then dried by a rotary evaporator under reduced pressure at 60° C. The dried product was dried in a drier at 120° C. overnight and then calcined in a muffle furnace at 650° C. for 3 hours, to obtain a platinum-supporting tin oxide catalyst containing 0.4 wt % of platinum.

1 ml of the catalyst thus prepared, was packed into a quartz tubular reactor having an inner diameter of 6.7 mm. Quartz chips were packed thereon. Then, while permitting hydrogen gas to flow through the tubular reactor at a flow rate of about 50 ml/min, the temperature was raised to 500° C., and then catalytic reduction treatment was carried out at the same temperature for one hour.

Reaction

Then, hydrogen was switched to nitrogen, and the interior of the reactor was sufficiently substituted by nitrogen, whereupon the gas mixture comprising styrene (hereinafter sometimes referred to as SM), ethylbenzene (hereinafter sometimes referred to as EB), water, hydrogen and air, was introduced into the tubular reactor to initiate the reaction.

The composition of the gas mixture was:
ethylbenzene/styrene/water/hydrogen/oxygen/nitrogen=1/1/12/1/0.52/1.95 (molar ratio).

Further, the space velocity in the reactor was:
SV=23,900 $hr^{-1}$ (calculated at 0° C. under 1 atm)
LHSV (ethylbenzene+styrene)=15 $hr^{-1}$ Upon expiration of 2 hours after initiation of the reaction, the gas at the outlet of the tubular reactor and the liquid trapped in a liquid receptor were analyzed by gas chromatography, whereby the hydrogen conversion was 96.6%, the oxygen conversion was 100%, the styrene and ethylbenzene combustion rate was 0.18%, and the benzene and toluene by-production rate was 0.12%. Here, the styrene and ethylbenzene combustion rate and the benzene and toluene by-production rate were calculated in accordance with the following equations.

Combustion rate (%) =

$$\frac{\{(\text{Produced CO} + \text{Produced CO}_2)/8\} \text{ (mol)}}{\text{Feed styrene} + \text{Feed ethylbenzene (mol)}} \times 100$$

By-production rate (%) =

$$\frac{\text{Produced benzene} + \text{Produced toluene (mol)}}{\text{Feed styrene} + \text{Feed ethylbenzene (mol)}} \times 100$$

EXAMPLE 2

The reaction was carried out in the same manner as in Example 1 except that the reaction temperature was changed to 400° C.

The hydrogen conversion was 99.7%, the oxygen conversion was 100%, the styrene and ethylbenzene combustion rate was 0.10%, and the benzene and toluene by-production rate was 0.08%.

EXAMPLE 3

The reaction was carried out in the same manner as in Example 1 except that the reaction temperature was changed to 600° C.

The hydrogen conversion was 87.1%, the oxygen conversion was 100%, the styrene and ethylbenzene combustion rate was 0.40%, and the benzene and toluene by-production rate was 0.27%.

EXAMPLE 4

The reaction was carried out in the same manner as in Example 1 using a platinum-supporting tin oxide catalyst containing 0.4 wt % of platinum, prepared in the same manner as in Example 1 except that tin oxide prepared by changing the calcination temperature to 800° C. or 1,200° C. was employed.

In the case where the calcination temperature of tin oxide was 800° C.

Hydrogen conversion: 94.1%, oxygen conversion: 100%, styrene and ethylbenzene combustion rate: 0.24%, and benzene and toluene by-production rate: 0.14%

In the case where the calcination temperature of tin oxide was 1,200° C.

Hydrogen conversion: 92.6%, oxygen conversion: 100%, styrene and ethylbenzene combustion rate: 0.27%, and benzene and toluene by-production rate: 0.00%

EXAMPLE 5

The catalyst was prepared and evaluated in the same manner as in Example 1 except that the amount of platinum supported was changed to 0.2 wt %, and the results are shown in Table 1.

TABLE 1

| Reaction temperature (° C.) | Hydrogen conversion (%) | Oxygen conversion (%) | SM*1 + EB*2 combustion rate (%) | BZ*3 + TOL*4 by-production rate (%) |
|---|---|---|---|---|
| 400 | 99.2 | 97.9 | 0.08 | 0.00 |
| 500 | 96.6 | 100 | 0.18 | 0.11 |

TABLE 1-continued

| Reaction temperature (° C.) | Hydrogen conversion (%) | Oxygen conversion (%) | SM*1 + EB*2 combustion rate (%) | BZ*3 + TOL*4 by-production rate (%) |
|---|---|---|---|---|
| 600 | 83.4 | 100 | 0.49 | 0.28 |

*1Styrene
*2Ethylbenzene
*3Benzene
*4Toluene

EXAMPLE 6

The catalyst was prepared and evaluated in the same manner as in Example 1 except that the amount of platinum supported was changed to 0.8 wt %, and the results are shown in Table 2.

TABLE 2

| Reaction temperature (° C.) | Hydrogen conversion (%) | Oxygen conversion (%) | SM*1 + EB*2 combustion rate (%) | BZ*3 + TOL*4 by-production rate (%) |
|---|---|---|---|---|
| 400 | 99.7 | 100 | 0.10 | 0.08 |
| 500 | 96.6 | 100 | 0.18 | 0.12 |
| 600 | 87.1 | 100 | 0.40 | 0.27 |

*1Styrene
*2Ethylbenzene
*3Benzene
*4Toluene

COMPARATIVE EXAMPLE 1

The catalyst was prepared and evaluated in the same manner as in Example 1 except that tin oxide in Example 1 was changed to α-$Al_2O_3$, and the results are shown in Table 3.

TABLE 3

| Reaction temperature (° C.) | Hydrogen conversion (%) | Oxygen conversion (%) | SM*1 + EB*2 combustion rate (%) |
|---|---|---|---|
| 500 | 87.0 | 100 | 0.40 |
| 600 | 67.1 | 100 | 0.88 |

*1Styrene
*2Ethylbenzene

EXAMPLE 7

Preparation of a Catalyst 500 ml of titanium isopropoxide was gradually added to 2 l of deionized water cooled by ice water to a temperature of not higher than 5° C. with stirring to form a hydroxide. The formed precipitate of titanium hydroxide was collected by filtration, washed with deionized water and then dried in a drier at 120° C. overnight. A small amount of deionized water was added to the dried product, and the mixture was kneaded for 3 hours and then extrusion-molded into pellets having a diameter of 3 mm. The molded product was dried in a drier at 120° C. overnight and further calcined in a muffle furnace at 1,200° C. for 3 hours.

The obtained titanium oxide was pulverized to a particle size of from 0.85 to 1.0 mm, and an aqueous solution of chloroplatinic acid in an amount corresponding to 0.4 wt % was uniformly added thereto, followed by drying under reduced pressure at 60° C. by a rotary evaporator. The dried product was further dried in a direr at 120° C. overnight and then calcined in a muffle furnace at 650° C. for 3 hours to obtain a 0.4 wt % Pt/TiO$_2$ catalyst.

Reaction 1 ml of the catalyst thus prepared was packed into a quartz tubular reactor having an inner diameter of about 7 mm and quartz chips having approximately the same particle size as the catalyst were packed on and under the catalyst. Then, while permitting a gas mixture of hydrogen and nitrogen to flow therethrough, reduction treatment was carried out at 500° C. for one hour. After the reduction treatment, the temperature of the catalyst layer was changed to a desired temperature under the same atmosphere, and then the interior of the reactor was substituted by nitrogen gas. Then, a gas mixture comprising styrene, ethylbenzene, water, hydrogen and air, was introduced into the tubular reactor, whereupon the reaction and evaluation were carried out in the same manner as in Example 1.

The results are shown in Table 4.

TABLE 4

| Reaction temperature (° C.) | Hydrogen conversion (%) | Oxygen conversion (%) | SM*[1] + EB*[2] combustion rate (%) |
| --- | --- | --- | --- |
| 400 | 97.4 | 100 | 0.16 |
| 500 | 92.3 | 100 | 0.28 |
| 600 | 82.3 | 100 | 0.52 |

*[1]Styrene
*[2]Ethylbenzene

EXAMPLE 8

Preparation of a Catalyst

A small amount of deionized water was added to 100 g of basic niobium hydroxide (NbO(OH)$_3$), and the mixture was kneaded for one hour and then extrusion-molded into pellets having a diameter of 3 mm. The molded product was dried in a drier at 120° C. overnight and further calcined in a muffle furnace at 1,000° C. for 3 hours.

The obtained niobium oxide molded product was pulverized to a particle size of from 0.85 to 1.0 mm, and an aqueous solution of chloroplatinic acid in an amount corresponding to 0.4 wt % of Pt was uniformly added thereto, followed by drying under reduced pressure at 60° C. by a rotary evaporator. The dried product was further dried by a drier at 120° C. overnight and calcined in a muffle furnace at 650° C. for 3 hours to obtain a 0.4 wt % Pt/Nb$_2$O$_5$ catalyst.

Reaction 1 ml of the catalyst thus prepared, was packed into a quartz tubular reactor having an inner diameter of about 7 mm, and quartz chips having approximately the same particle size as the catalyst were packed on and under the catalyst. Then, while permitting a gas mixture of hydrogen and nitrogen to flow therethrough, reduction treatment was carried out at 500° C. for one hour. After the reduction treatment, the temperature of the catalyst layer was changed to a desired temperature under the same atmosphere, and then the interior of the reactor was substituted by nitrogen gas. Then, a gas mixture comprising styrene, ethylbenzene, water, hydrogen and air, was introduced into the tubular reactor, whereupon the reaction and evaluation were carried out in the same manner as in Example 1.

The results are shown in Table 5.

TABLE 5

0.4 wt % Pt/Nb$_2$O$_5$ catalyst

| Reaction temperature (° C.) | Hydrogen conversion (%) | Oxygen conversion (%) | SM*[1] + EB*[2] combustion rate (%) |
| --- | --- | --- | --- |
| 500 | 97.1 | 98.5 | 0.13 |
| 600 | 86.8 | 100 | 0.41 |

*[1]Styrene
*[2]Ethylbenzene

EXAMPLE 9

Preparation of a Catalyst

A small amount of deionized water was added to 100 g of tantalum oxide (Ta$_2$O$_5$), and the mixture was kneaded for one hour and then extrusion-molded into pellets having a diameter of 3 mm. The molded product was dried in a drier at 120° C. overnight and further calcined in a muffle furnace at 1,000° C. for 3 hours.

The obtained tantalum oxide molded product was pulverized to a particle size of from 0.85 to 1.0 mm, and an aqueous solution of chloroplatinic acid in an amount corresponding to 0.4 wt % of Pt was uniformly added thereto, followed by drying under reduced pressure at 60° C. by a rotary evaporator. The dried product was further dried in a drier at 120° C. overnight and then calcined in a muffle furnace at 650° C. for 3 hours. to obtain a 0.4 wt % Pt/Ta$_2$O$_5$ catalyst.

Reaction 1 ml of the catalyst thus prepared, was packed into a quartz tubular reactor having an inner diameter of about 7 mm, and quartz chips having approximately the same particle size as the catalyst were packed on and under the catalyst. Then, while permitting a gas mixture of hydrogen and nitrogen to flow therethrough, reduction treatment was carried out at 500° C. for one hour. After the reduction treatment, the temperature of the catalyst layer was changed to a desired temperature, and then the interior of the reactor was substituted by nitrogen gas. Then, a gas mixture comprising styrene, ethylbenzene, water, hydrogen and air, was introduced into the tubular reactor, whereupon the reaction and evaluation were carried out in the same manner as in Example 1.

The results are shown in Table 6.

TABLE 6

0.4 wt % Pt/Ta$_2$O$_5$ catalyst

| Reaction temperature (° C.) | Hydrogen conversion (%) | Oxygen conversion (%) | SM*[1] + EB*[2] combustion rate (%) |
| --- | --- | --- | --- |
| 400 | 98.4 | 100 | 0.08 |
| 500 | 94.3 | 100 | 0.23 |
| 600 | 83.9 | 100 | 0.47 |

*[1]Styrene
*[2]Ethylbenzene

EXAMPLE 10

Preparation of a Catalyst 3N aqueous ammonia was gradually added to an aqueous stannous chloride solution with stirring to form a precipitate of a hydroxide. When the pH exceeded 7, addition of aqueous ammonia was stopped, and the formed precipitate of tin hydroxide was collected by filtration, washed with deionized water and then dried in a drier at 120° C. overnight. The dried precipitate was calcined in a muffle furnace at 600° C. for 3 hours.

A small amount of deionized water was added to the calcined product, and the mixture was kneaded for one hour and extrusion-molded into pellets having a diameter of 3 mm. The molded product was dried in a drier at 120° C. overnight and further calcined in a muffle furnace at 1,000° C. for 3 hours.

The obtained tin oxide was pulverized to a particle size of from 0.85 to 1.0 mm, and a hydrochloric acid aqueous solution of palladium chloride in an amount corresponding to 0.4 wt % of palladium, was uniformly added thereto, followed by drying under reduced pressure at 60° C. by a rotary evaporator. The dried product was further dried in a drier at 120° C. overnight and then calcined in a muffle furnace at 550° C. for 3 hours to obtain a 0.4 wt % Pd/SnO$_2$ catalyst.

Reaction 1 ml of the catalyst thus prepared, was packed into a quartz tubular reactor having an inner diameter of about 7 mm, and quartz chips having approximately the same particle size as the catalyst were packed on and under the catalyst. Then, while permitting a gas mixture of hydrogen and nitrogen to flow therethrough, reduction treatment was carried out at 500° C. for one hour. After the reduction treatment, the temperature of the catalyst layer was changed to a desired temperature, and the interior of the reactor was substituted by nitrogen gas. Then, a gas mixture comprising styrene, ethylbenzene, water, hydrogen and air, was introduced into the tubular reactor, whereupon the reaction and evaluation were carried out in the same manner as in Example 1.

The results are shown in Table 7.

TABLE 7

0.4 wt % Pd/SnO$_2$ catalyst

| Reaction temperature (° C.) | Hydrogen conversion (%) | Oxygen conversion (%) | SM$^{*1}$ + EB$^{*2}$ combustion rate (%) | BZ$^{*3}$ + TOL$^{*4}$ by-production rate (%) |
|---|---|---|---|---|
| 400 | 96.1 | 100 | 0.18 | 0.20 |
| 500 | 87.9 | 100 | 0.38 | 0.21 |
| 600 | 78.3 | 100 | 0.61 | 0.25 |

*$^1$Styrene
*$^2$Ethylbenzene
*$^3$Benzene
*$^4$Toluene

EXAMPLE 11

The catalyst was prepared and evaluated in the same manner as in Example 10 except that the amount of palladium supported, was changed to 1.0 wt %, and the results are shown in Table 8.

TABLE 8

1.0 wt % Pd/SnO$_2$ catalyst

| Reaction temperature (° C.) | Hydrogen conversion (%) | Oxygen conversion (%) | SM$^{*1}$ + EB$^{*2}$ combustion rate (%) | BZ$^{*3}$ + TOL$^{*4}$ by-production rate (%) |
|---|---|---|---|---|
| 400 | 95.8 | 100 | 0.20 | 0.18 |
| 500 | 88.0 | 100 | 0.38 | 0.20 |
| 600 | 81.5 | 100 | 0.54 | 0.24 |

*$^1$Styrene
*$^2$Ethylbenzene
*$^3$Benzene
*$^4$Toluene

COMPARATIVE EXAMPLE 2

Preparation of a Catalyst 50 g of precipitated and dried SnO$_2$ was mixed with 18.59 g of 10 vol % HNO$_3$ for 15 minutes and then 43.24 g of a Pd(NO$_3$)$_2$ solution having a Pd content of 3.43 wt % was added slowly to the above mixture. Mixing was continued for 30 minutes in a mixer and then 1.064 g of a H$_2$PtCl$_6$.6H$_2$O solution having a Pt content of 4.89 wt % was added to the mixture. Mixing was continued for another 30 minutes. The resultant mixture was then dried at 105° C. for 10 hours. The dried product was mixed with a small amount of deionized water for 60 minutes and was then extrusion-molded into pellets having an average diameter of 3 mm. The pellets were dried at 105° C. for 3 hours and calcined in air at 350° C. for 4 hours to obtain a catalyst.

Reaction

The catalyst obtained above was crushed to 0.8–1.0 mm, and 1 ml of the catalyst was packed into a quartz tubular reactor having an inner diameter of about 7 mm. The catalyst was packed between upper and lower layers of quartz chips of the same particle diameter. Then, the temperature of the catalyst layer was raised to a predetermined value while nitrogen gas was passed through the reactor. Then, a gas mixture comprising ethylbenzene (EB), styrene (SM), water, air and hydrogen, was introduced into the tubular reactor to initiate the reaction. The composition of the gas mixture was: EB/SM/H$_2$O/H$_2$/O$_2$/N$_2$=1/1/12/1/0.52/1.95 (molar ratio).

The space velocity in the reactor was:
SV=23,900 hr$^{-1}$ (calculated at 0° C. under 1 atm)
LHSV (EB+SM)=15 hr$^{-1}$ The results are shown in the following Table 9.

TABLE 9

| Reaction temperature (° C.) | Hydrogen conversion (%) | Oxygen conversion (%) | SM$^{*1}$ + EB$^{*2}$ combustion rate (%) | BZ$^{*3}$ + TOL$^{*4}$ by-production rate (%) |
|---|---|---|---|---|
| 400 | 97.3 | 100 | 0.18 | 0.35 |
| 500 | 88.3 | 100 | 0.38 | 0.55 |
| 600 | 76.4 | 100 | 0.64 | 0.63 |

*$^1$Styrene
*$^2$Ethylbenzene
*$^3$Benzene
*$^4$Toluene

COMPARATIVE EXAMPLE 3

Preparation of a Catalyst 39.8 g of $SnO_2$ powder calcined at 350° C. for 4 hours was slurried with 15.74 ml of 10 vol % $HNO_3$, and the mixture was stirred for 10 minutes. Tetramine palladium nitrate aqueous solution containing 5 wt % of Pd was added to the slurry and stirred for 30 minutes. The slurry was then dried and was further dried in a tray overnight at 105° C. The dried powder was calcined in air at 350° C. for 1 hour, then mixed with a small amount of deionized water, mashed for 1 hour, and extrusion-molded into pellets having an average diameter of 3 mm. The pellets were dried at 105° C. overnight and then calcined in air at 350° C. for 2 hours and further at 600° C. for 4 hours to obtain a catalyst.

Reaction

The reaction was carried out in the same manner as in Comparative Example 2, except for using the above prepared catalyst.

The results are shown in the following Table 10.

TABLE 10

| Reaction temperature (° C.) | Hydrogen conversion (%) | Oxygen conversion (%) | $SM^{*1} + EB^{*2}$ combustion rate (%) | $BZ^{*3} + TOL^{*4}$ by-production rate (%) |
|---|---|---|---|---|
| 400 | 99.2 | 100 | 0.14 | 0.38 |
| 500 | 92.8 | 100 | 0.28 | 0.46 |
| 600 | 82.7 | 100 | 0.50 | 0.45 |

*¹Styrene
*²Ethylbenzene
*³Benzene
*⁴Toluene

COMPARATIVE EXAMPLE 4

Preparation of a Catalyst

Extrusion-molded $SnO_2$ pellets calcined at 350° C. for 4 hours were crushed to a particle size of from 0.8 to 1.0 mm. To 13.1411 g of the crushed material, was added 2.5663 g of 2.0565 wt % $H_2PtCl_6.6H_2O$ solution. The resulting slurry was rotary-evaporated and then dried in a tray at 105° C. overnight. The dried product was then calcined in flowing air according to the profile to obtain Cat-3:

50–150° C., at a temperature rise of 100° C./hr, for 2 hours

150–350° C., at a temperature rise of 100° C./hr, for 2 hours

350–600° C., at a temperature rise of 100° C./hr, for 4 hours

Reaction

The reaction was carried out in the same manner as in Comparative Example 2, except for using the above prepared catalyst.

The results are shown in the following Table 11.

TABLE 11

| Reaction temperature (° C.) | Hydrogen conversion (%) | Oxygen conversion (%) | $SM^{*1} + EB^{*2}$ combustion rate (%) | $BZ^{*3} + TOL^{*4}$ by-production rate (%) |
|---|---|---|---|---|
| 400 | 98.7 | 97.2 | 0.06 | 0.19 |
| 500 | 95.6 | 100 | 0.20 | 0.25 |
| 600 | 87.5 | 100 | 0.39 | 0.41 |

*¹Styrene
*²Ethylbenzene
*³Benzene
*⁴Toluene

As shown by the foregoing Examples, by the method of the present invention, hydrogen can selectively be oxidized, and the loss due to combustion of a co-existing hydrocarbon, can be suppressed to such a sufficiently low level that there will be substantially no problem.

What is claimed is:

1. A method for the dehydrogenation of a hydrocarbon which comprises (1) dehydrogenating a hydrocarbon feed in the presence of a dehydrogenation catalyst to form a gas mixture including a dehydrogenated hydrocarbon, an unreacted feed hydrocarbon and hydrogen, (2) contacting said mixture with an oxygen containing gas in the presence of an oxidation catalyst comprising at least one component selected from the group consisting of platinum and palladium, supported on a carrier obtained by calcining, at a temperature of from 800° C. to 1,500° C., at least one member selected from the group consisting of tin oxide, titanium oxide, tantalum oxide and niobium oxide to selectively oxidize said hydrogen, and (3) further subjecting a hydrocarbon containing gas formed in (2) to a second dehydrogenation reaction.

2. The method according to claim 1, wherein a catalyst comprising a component having platinum supported on tin oxide, is used as the oxidation catalyst.

3. The method according to claim 1, wherein a catalyst comprising a component having platinum supported on titanium oxide, is used as the oxidation catalyst.

4. The method according to claim 1, wherein a catalyst comprising a component having platinum supported on tantalum oxide, is used as the oxidation catalyst.

5. The method according to claim 1, wherein a catalyst comprising a component having platinum supported on niobium oxide, is used as the oxidation catalyst.

6. The method according to claim 1, wherein a catalyst comprising a component having palladium supported on tin oxide, is used as the oxidation catalyst.

7. The method according to claim 1, wherein the feed hydrocarbon is ethylbenzene, and the dehydrogenated hydrocarbon is styrene.

\* \* \* \* \*